United States Patent [19]
Coughlin et al.

[11] Patent Number: 5,308,843
[45] Date of Patent: May 3, 1994

[54] METHOD OF INHIBITING MAMMALIAN TOPOISOMERASE II AND MALIGNANT CELL GROWTH IN MAMMALS, WITH SUBSTITUTED (S)-3-METHYL-7-OXO-2,3-DIHYDRO-7H-PYRIDO[1,2,3-DE][1,4]-BENZOXAZINE(AND-BENZOTHIAZINE)-6-CARBOXYLIC ACIDS

[75] Inventors: Susan Coughlin, Chatham, N.Y.; George Y. Lesher, deceased, late of Schodack, N.Y., by Louise Elliot Lesher, executor; James B. Rake, Halfmoon; Mark P. Wentland, Colonie, both of N.Y.

[73] Assignee: Sterling Drug Inc., New York, N.Y.

[21] Appl. No.: 580,732

[22] Filed: Sep. 11, 1990

[51] Int. Cl.$^5$ .................. A61K 31/535; A61K 31/54; C07D 279/18; C07D 265/38
[52] U.S. Cl. .................. 514/227.8; 514/230.2; 544/32; 544/101
[58] Field of Search .............. 544/101, 32; 514/227.8, 514/224.5, 230.2

[56] References Cited

U.S. PATENT DOCUMENTS

| | | | |
|---|---|---|---|
| 4,382,892 | 5/1983 | Hayakawa et al. | 540/575 |
| 4,540,694 | 9/1985 | Chu | 514/232 |
| 4,571,396 | 2/1986 | Hutt et al. | 514/249 |
| 4,623,650 | 11/1986 | Gilligan et al. | 514/312 |
| 4,636,506 | 1/1987 | Gilligan et al. | 514/256 |
| 4,668,784 | 5/1987 | Mascellani et al. | 544/32 |
| 4,839,355 | 6/1989 | Lesher | 514/224.5 |

OTHER PUBLICATIONS

Abramovitch, Pyridine and Its Derivatives Supplement, Part Two, pp. 5–15, Wiley Interscience Publishers (1974).
M. R. Jefson et al., Paper presented at the 29th Interscience Conference on Antimicrobial Agents and Chemotherapy, Sep. 17–21, 1989, Houston, Texas.
K. Hoshino et al., Antimicrobial Agents and Chemotherapy, 33(10), 1816–1818 (Oct. 1989).
P. Hussy et al., Antimicrobial Agents and Chemotherapy, 29(6), 1073–1078 (Jun. 1986).
J. F. Barrett et al., Paper presented at the 27th Interscience Conference on Antimicrobial Agents and Chemotherapy, Oct. 4–7, 1987, New York, New York.
J. F. Barrett et al., Antimicrobial Agents and Chemotherapy, 33(10), 1697–1703 (Oct. 1989).

*Primary Examiner*—Alan L. Rotman
*Attorney, Agent, or Firm*—Liza D. Hohenschutz

[57] ABSTRACT

A method of inhibiting mammalian topoisomerase II and inhibiting the growth and inducing the regression of malignant cells in mammals by the action of a (S)-3-methyl-7-oxo-2,3-dihydro-7H-pyrido[1,2,3-de][1,4]benzoxazine or -benzothiazine of the formula

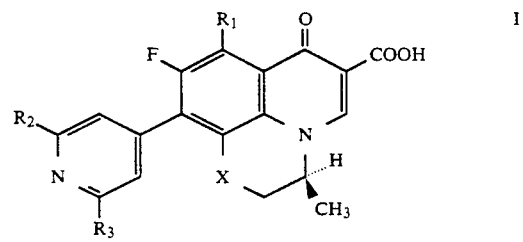

wherein $R_1$ is hydrogen or fluoro, $R_2$ and $R_3$ each independently is hydrogen or alkyl having 1 to 4 carbon atoms, and X is O, S or S=O; a pharmaceutically acceptable acid-addition salt thereof; or a salt thereof with a pharmaceutically acceptable cation; and certain novel compounds of formula I.

7 Claims, No Drawings

METHOD OF INHIBITING MAMMALIAN TOPOISOMERASE II AND MALIGNANT CELL GROWTH IN MAMMALS, WITH SUBSTITUTED (S)-3-METHYL-7-OXO-2,3-DIHYDRO-7H-PYRIDO[1,2,3-DE][1,4]-BENZOXAZINE(AND-BENZOTHIAZINE)-6-CARBOXYLIC ACIDS

BACKGROUND OF THE INVENTION a) Field of the Invention

The invention relates to the inhibition of mammalian topoisomerase II and of the growth of malignant cells and to inducing the regression of malignant cells in mammals by the action of certain (S)-3-methyl-7-oxo-2,3-dihydro-7H-pyrido[1,2,3-de][1,4]benzoxazine(and benzothiazine)-6-carboxylic acids; and to certain of such compounds which are novel.

b) Information Disclosure Statement

Hayakawa et al. U.S. Pat. No. 4,382,892, issued May 10, 1983, discloses antibacterial pyrido[1,2,3-de][1,4-]benzoxazine derivatives having the formula

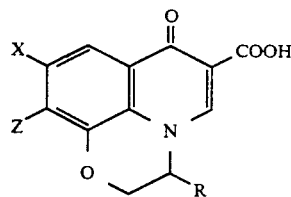

wherein X is a halogen atom, R is a hydrogen atom or an alkyl group of 1 to 6 carbon atoms and Z represents mono-substituted, di-substituted or cyclic-substituted amino group which may contain a hetero atom and may have a substituent such as hydroxyl, alkyl having 1 to 6 carbon atoms, amino, hydroxyalkyl having 1 to 6 carbon atoms or mono- or di-alkylamino having 1 to 6 carbon atoms in each alkyl moiety.

D. T. Chu U.S. Pat. No. 4,540,694, issued Sep. 10, 1985, discloses antibacterial pyridine-substituted quino-benzoxazines having the formula

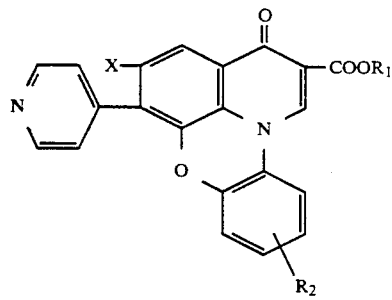

wherein X is halogen or hydrogen; $R_2$ is a substituent; and $R_1$ is hydrogen or a carboxy protecting group. The specification of the patent suggests substitution on the pyridine ring including alkyl groups but there are no specific examples thereof.

Hutt et al. U.S. Pat. No. 4,571,396, issued Feb. 18, 1986, discloses antibacterial quinolones which include compounds of the formula

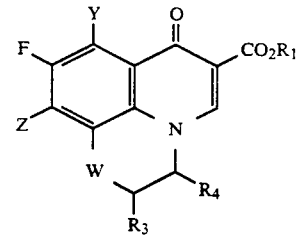

wherein $R_1$ is hydrogen, $C_{1-6}$ alkyl or a cation, Y is hydrogen, fluoro or amino, W is O, NR, S or CH, $R_3$ and $R_4$ are hydrogen or $C_{1-3}$ alkyl, and Z is an aza- or diazabicycloalkyl radical.

Gilligan et al. U.S. pat. No. 4,623,650, issued Nov. 18, 1986 discloses antibacterial quinolones of the formula

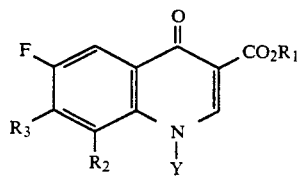

wherein $R_1$ is hydrogen, alkyl of 1 to 6 carbon atoms, benzyl or a pharmaceutically acceptable cation; $R_2$ is hydrogen or fluoro; $R_2$ and Y, inter alia, when taken together have the formula —X—$(CH_2)_n$—$CHR_4$— wherein X is $CH_2$, O, S, NH or $NCH_3$, n is 0, 1 or 2, and $R_4$ is selected from the group consisting of hydrogen, alkyl and haloalkyl of 1 to 3 carbons, hydroxymethyl, hydroxyethyl, aminomethyl, phenyl and methylene; and $R_3$ is phenyl which may be substituted by one to three defined substituents including $C_{1-4}$ alkyl. The only specific compounds disclosed where $R_2$ and Y are —X—$(CH_2)_n$—$CHR_4$— are Example 43 ($R_1$=H, $R_3$=phenyl, X=O, n=1, and $R_4$=$CH_3$) and Example 44 ($R_1$=H, $R_3$=4-aminosulfonylphenyl, X=O, n=1, and $R_4$=$CH_3$).

Gilligan et al. U.S. Pat. No. 4,636,506, issued Jan. 13, 1987, discloses antibacterial quinolones of the formula

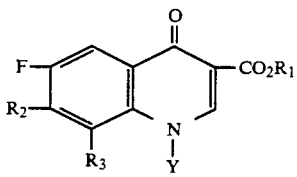

wherein $R_1$ is hydrogen, a pharmaceutically acceptable cation or alkyl of 1 to 3 carbon atoms; $R_2$ is 3-pyridyl or 4-pyridyl which may be substituted by various groups not including alkyl; and, inter alia, $R_3$ and Y may be combined to form a bridge of the formula —X($CH_2$)$_n$—$CHR_4$— or —X($CH_2$)$_n$—C(=$CH_2$)— wherein X is $CH_2$, O, S, NH or $NCH_3$; n is 0, 1 or 2, and $R_4$ is selected from the group consisting of hydrogen, alkyl and halo alkyl of 1 to 3 carbon atoms, hydroxymethyl, hydroxyethyl, aminoethyl and phenyl. The only specific compounds disclosed where $R_3$ and Y are combined are Example 7 ($R_1$=H, $R_2$=3-pyridyl, and combined $R_3$ and Y=—S—$CH_2$—$CH_2$—) and Example 8 ($R_1$=H, $R_2$=3-pyridyl, and combined $R_3$ and Y=—N($CH_3$)—$CH_2$—$CH_2$—).

Lesher U.S. Pat. No. 4,839,355, issued Jun. 13, 1989, discloses antibacterial fluorinated 10-(2,6-dimethyl-4-pyridinyl)-7-oxo-2,3-dihydro-7H-pyrido[1,2,3-de][1,4-]benzoxazine-6-carboxylic acids and -benzothiazine-6-carboxylic acids of the formula

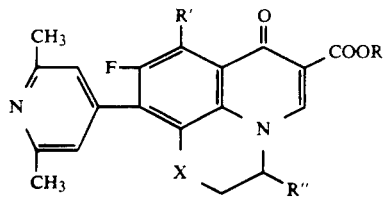

wherein R is hydrogen, R' is hydrogen or fluoro, R" is alkyl of 1-3 carbon atoms and X is O or S.

M. R. Jefson et al., at the 29th Interscience Conference on Antimicrobial Agents and Chemotherapy held Sep. 17-20, 1989, disclosed the synthesis and properties of optically pure $C_7$-heteroaryl quinolones structurally related to ofloxacin. Included in the properties studied was the in vitro DNA gyrase and mammalian topoisomerase activities of S-(−)-CP-92,121 [(S)-9-fluoro-3-methyl-10-(4-pyridyl)-7-oxo-7H-pyrido[1,2,3-de][1,4-]benzoxazine-6-carboxylic acid] and its antipode, R-(+)-CP-91,120; and S-(−)-CP-100,964 [(S)-9-fluoro-3-methyl-10-(6-quinolyl)-7-oxo-7H-pyrido[1,2,3-de][1,4]benzoxazine-6-carboxylic acid] and its antipode, R-(+)-CP-100,965. The calf thymus topoisomerase II activities, expressed as $CC_{50}$s (µg/ml), for these compounds was 30, 380, 20 and >1000 respectively. It is stated that the combined potent activity against procaryotic and eucaryotic topoisomerase enzymes make agents such as CP-92,121 and CP-100,964 attractive compounds for potential use as cancer chemotherapeutants.

K. Hoshino et al., Antimicrobial Agents and Chemotherapy, 33(10), 1816-1818 (October 1989) compared the in vitro inhibitory effect of certain quinolones on bacterial DNA gyrase of Escherichia coli KL-16 and topoisomerase II of fetal calf thymus. Included in the comparison are ofloxacin [9-fluoro-3-methyl-10-(4-methyl-1-piperazinyl)-7-oxo-2,3-dihydro-7H-pyrido[1,2,3-de][1,4]benzoxazine-6-carboxylic acid], fleroxacin [6,8-difluoro-1-(2-fluoroethyl)-7-(4-methyl-1-piperazinyl)-1,4-dihydro-4-oxo-3-quinolinecarboxylic acid], ciprofloxacin [1-cycloproyl-6-fluoro-7-(1-piperazinyl)-1,4-dihydro-4-oxo-3-quinolinecarboxylic acid], CI-934 [6,8-difluoro-1-ethyl-7-[3-(ethylaminomethyl)-1-pyrrolidinyl]-1,4-dihydro-4-oxo-3-quinolinecarboxylic acid] and lomefloxacin [6,8-difluoro-1-ethyl-7-(3-methyl-1-piperazinyl)-1,4-dihydro-4-oxo-3-quinolinecarboxylic acid], the 50% inhibitory doses for topoisomerase II of which were found to vary between 64 and 1,870 µg/ml, the potency of inhibition being lowest for ofloxacin.

P. Hussy et al., Antimicrobial Agents and Chemotherapy, 29(6), 1073-1078 (June 1986) investigated the effect of certain 4-quinolones and novobiocin on elements of eucaryotic DNA replication in vitro. Ciprofloxacin, norfloxacin [1-ethyl-6-fluoro-7-(1-piperazinyl)-1,4-dihydro-4-oxo-3-quinolinecarboxylic acid] and ofloxacin were included in the investigation and found to have $K_i$ values of 50% inhibition of DNA topoisomerases from calf thymus of 150, 300 and 1300 µg/ml respectively in the case of topoisomerase II.

J. F. Barrett et al., at the 27th Interscience Conference on Antimicrobial Agents and Chemotherapy held Oct. 4 to 7, 1987, disclosed that several quinolones and anti-tumor compounds were tested as inhibitors of purified eukaryotic topoisomerase II in unknotting, catenation and radiolabeled DNA cleavage assays. Among the quinolones tested, ciprofloxacin and norfloxacin were reported not to be potent enhancers of DNA cleavage mediated by topoisomerase II whereas, in contrast, CP-67,015 [6,8-difluoro-1-ethyl-7-(4-pyridyl)-1,4-dihydro-4-oxo-3-quinolinecarboxylic acid] induced significant DNA cleavage in both the radiolabeled and cold cleavage assays [see also J. F. Barrett et al., Antimicrobial Agents and Chemotherapy, 33(10), 1697-1703 (October 1989)].

SUMMARY OF THE INVENTION

The invention resides in one aspect in a method of inhibiting mammalian topoisomerase II in a mammal which comprises administering to the mammal a compound which is a (S)-3-methyl-7-oxo-2,3-dihydro-7H-pyrido[1,2,3-de][1,4]benzoxazine or -benzothiazine of the formula

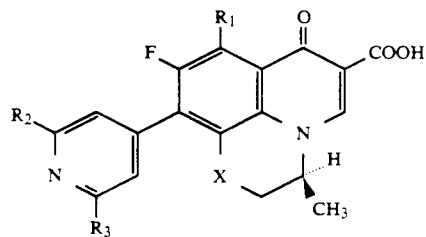

wherein $R_1$ is hydrogen or fluoro, $R_2$ and $R_3$ each independently is hydrogen or alkyl having 1 to 4 carbon atoms, and X is O, S or S=O; a pharmaceutically acceptable acid-addition salt thereof; or a salt thereof with a pharmaceutically acceptable cation; the compound being administered in a therapeutic amount which is effective to inhibit the mammalian topoisomerase II.

In a second aspect, the invention resides in a method of inhibiting the growth of or killing malignant cells in a mammal afflicted with malignant cells which comprises administering to the mammal a compound which is a (S)-3-methyl-7-oxo-2,3-dihydro-7H-pyrido[1,2,3-de][1,4]benzoxazine or -benzothiazine of formula I above; a pharmaceutically acceptable acid-addition salt thereof; or a salt thereof with a pharmaceutically acceptable cation; the malignant cells being susceptible to the action of the compound, and the compound being administered in a therapeutic amount which is effective to inhibit the growth of or kill the malignant cells.

A third aspect of the invention resides in a method of inhibiting the growth or inducing the regression of cells of a tumor in a mammal afflicted with the tumor which comprises administering to the mammal a compound which is a (S)-3-methyl-7-oxo-2,3-dihydro-7H-pyrido[1,2,3-de][1,4]benzoxazine or -benzothiazine of formula I above; a pharmaceutically acceptable acid-addition salt thereof; or a salt thereof with a pharmaceutically effective cation; the tumor cells being susceptible to the action of the compound, and the compound being administered in a therapeutic amount which is effective to inhibit the growth or induce the regression of the tumor cells.

In a fourth aspect the invention resides in novel compounds selected from the group consisting of (S)-10-(4- pyridinyl)-9-fluoro-2,3-dihydro-3-methyl-7-oxo-7H-pyrido[1,2,3-de][1,4]benzoxazine-6-carboxylic acid, (S)-10-(2-ethyl-6-methyl-4-pyridinyl)-9-fluoro-2,3-dihydro-3-methyl-7-oxo-7H-pyrido[1,2,3-de][1,4]benzoxazine-6-carboxylic acid, (S)-10-(2-ethyl-4-pyridinyl)-9-fluoro-2,3-dihydro-3-methyl-7-oxo-7H-pyrido[1,2,3-de][1,4]benzoxazine-6-carboxylic acid, (S)-10-(2,6-dimethyl-4-pyridinyl)-9-fluoro-3-methyl-7-oxo-2,3-dihydro-7H-pyrido[1,2,3-de][1,4]benzothiazine-6-carboxylic acid 1-oxide; a pharmaceutically acceptable acid-addition salt of said compounds; and a salt of said compounds with a pharmaceutically acceptable cation.

DETAILED DESCRIPTION INCLUSIVE OF THE PREFERRED EMBODIMENTS

The term "alkyl" as used herein refers to alkyl having from 1 to 4 carbon atoms which may be straight chain or branched chain.

The term "mammal" as used herein refers both to human and non-human mammals.

The invention also contemplates pharmaceutically acceptable acid-addition salts of the compounds of formula I. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like.

The compounds of formula I, by virtue of the carboxylic acid moiety, can also be prepared and used in the form of a salt with a pharmaceutically acceptable cation such as alkali metal salts and amine salts, including but not limited to the sodium, potassium, ethylenediamine and N-methylglucamine salts.

The compounds of formula I where X is O or S are prepared by the synthetic procedures described in U.S. Pat. No. 4,839,355, the disclosure of which is incorporated herein by reference.

The compounds of formula I where X is S=O are prepared from the corresponding compounds where X is S by conventional oxidation with an organic peroxy acid such as peracetic acid, perbenzoic acid and m-chloroperbenzoic acid, or an inorganic peroxy salt such as potassium monopersulfate.

The following examples are illustrative of compounds employed in the method of the invention and include novel compounds of the invention.

The structures of the compounds were established by the modes of synthesis, by elementary analyses and by infrared, nuclear magnetic resonance and/or mass spectra.

EXAMPLE 1

(a) Ethyl (S)-10-(4-pyridinyl)-9-fluoro-2,3-dihydro-3-methyl-7-oxo-7H-pyrido[1,2,3-de][1,4]benzoxazine-6-carboxylate Ethyl (S)-10-bromo-9-fluoro-2,3-dihydro-3-methyl-7-oxo-7H-pyrido[1,2,3-de][1,4]benzoxazine-6-carboxylate (U.S. Pat. No. 4,839,355, Example 5f) (3.50 g), 2.97 g of 4-(trimethylstannyl)pyridine and 0.155 g of dichlorobis(triphenylphosphine)palladium were combined in a Parr apparatus in 200 ml of absolute ethyl alcohol and the mixture under nitrogen was heated at 150° C. for 4½ hours, allowed to cool slowly and concentrated in vacuo. The concentrate was taken up in chloroform and residues were removed by filtration. The filtrate was extracted with sufficient 1M hydrochloric acid to extract all the product and the aqueous extract was poured onto ice and saturated sodium acetate was added. The resulting mixture was extracted with chloroform and the chloroform extract was washed with brine followed by sodium bicarbonate, dried over magnesium sulfate and concentrated to give, after recrystallization from acetonitrile, 2.56 g of a mixture of the title compound with its corresponding 6-carboxylic acid (73.5% yield); m.p. 249°–252° C. This was combined with 100 mg of the same product obtained previously by an analogous procedure.

(b) (S)-10-(4-Pyridinyl)-9-fluoro-2,3-dihydro-3-methyl-7-oxo-7H-pyrido[1,2,3-de][1,4]benzoxazine-6-carboxylic acid [I; $R_1$, $R_2$ and $R_3$=H, X=O]

To 20 ml of 1M hydrochloric acid there was added 2.65 g of the mixture containing ethyl (S)-10-(4-pyridinyl)-9-fluoro-2,3-dihydro-3-methyl-7-oxo-7H-pyrido[1,2,3-de][1,4]benzoxazine-6-carboxylate and its corresponding 6-carboxylic acid from (a) above and the mixture was heated at reflux for 3 hours. The mixture was poured onto ice and sodium acetate was added to neutralize the product. The precipitate was collected by filtration to give, after recrystallization from acetonitrile, with charcoal treatment, 1.3 g of the title compound (53.1% yield); m.p. 343°–345° C.

EXAMPLE 2

(a) 4-Bromo-2-ethyl-6-methylpyridine

2-Ethyl-6-methyl-4-nitropyridine N-oxide (36.4 g) was added to 60 g of acetic acid and the mixture was warmed to give a clear solution which was cooled to 15°–20° C. and treated dropwise, keeping the temperature below 25° C., with 49.2 g of acetyl bromide. After addition was complete, the mixture was stirred at room temperature for 1½ hours and then slowly warmed to 65°–70° C. and kept in this temperature range for 24 hours. The acetic acid and volatile components were removed in vacuo and 200 ml of chloroform were added to the residue. To the chilled mixture there was added dropwise 58 g of phosphorus tribromide at 10° C. and the mixture was warmed to room temperature and then heated at reflux for 3 hours. An additional 10 g of phosphorus tribromide were added and the mixture was heated for 1 hour, poured onto ice, neutralized with cold 35% sodium hydroxide and extracted three times with 200 ml of methylene chloride. The organic extract was concentrated, 300 ml of diethyl ether were added and the ether solution was dried over magnesium sulfate and concentrated. The crude product was fractionated in vacuo to give 30 g of the title product as a yellow oil; $bp_{13}$ 120°–130° C.

(b) 2-Ethyl-6-methyl-4-(tributylstannyl)pyridine

To a solution of 19.4 g of 4-bromo-2-ethyl-6-methylpyridine from (a) above in 275 ml of diethyl ether chilled to −70° C. under argon was added dropwise over ½ hour 38.8 ml of n-butyllithium while maintaining the reaction temperature below −65° C. Stirring was continued at −70° C. for 1 hour and then 22 ml (26.4 g) of tributyltin chloride in 25 ml of diethyl ether were added over 20 minutes. The mixture was allowed to warm to 20° C. and 200 ml of water was added. The ether layer was separated, dried over magnesium sulfate and concentrated in vacuo (90° C.; 50 mm). Hexane was added and the mixture was filtered and the filtrate was concentrated in vacuo (15 mm) to give the title product as a yellow liquid.

(c) Mixed ester (ethyl and butyl) of (S)-10-bromo-9-fluoro-2,3-dihydro-3-methyl-7-oxo-7H-pyrido[1,2,3-de][1,4]benzoxazine-6-carboxylic acid To 200 ml of acetonitrile under nitrogen and at reflux there was added 13.1 g of ethyl (S)-10-amino-9-fluoro-2,3-dihydro-3-methyl-7-oxo-7H-pyrido[1,2,3-de][1,4-]benzoxazine-6-carboxylate (U.S. Pat. No. 4,839,355, Example 5e), 11.15 g of cupric bromide and 7.47 ml of n-butyl nitrite at a rate which maintained gentle reflux. Addition time was about 10 minutes. Heating at reflux was continued for 2½ hours and the mixture was allowed to cool and then was poured into 1 liter of water containing 100 ml of concentrated ammonium hydroxide. The resulting precipitate was collected by filtration to give 13 g of the title mixed ester as a tan solid.

(d) (S)-10-(2-Ethyl-6-methyl-4-pyridinyl)-9-fluoro-2,3-dihydro-3-methyl-7-oxo-7H-pyrido[1,2,3-de][1,4-]benzoxazine-6-carboxylic acid [I; $R_1=H$, $R_2=C_2H_5$, $R_3=CH_3$, $X=O$]

The mixed ester of (S)-10-bromo-9-fluoro-2,3-dihydro-3-methyl-7-oxo-7H-pyrido[1,2,3-de][1,4]benzoxazine-6-carboxylic acid from (c) above (2.0 g), 3.1 g of 2-ethyl-6-methyl-4-(tributylstannyl)pyridine from (b) above and 300 mg of dichlorobis(triphenylphosphine)-palladium were combined in 2 ml of dimethylformamide under nitrogen and heated at 150° C. for 3 hours. Chloroform (25 ml) and 1 ml of water were added and the mixture was filtered and the filtrate was concentrated to dryness. To the resulting residue was added 20 ml of 6N hydrochloric acid, the mixture was filtered, the filtrate was concentrated and product was precipitated by the addition of potassium carbonate. To the resulting mixture there was added 20 ml of 4N hydrochloric acid and the mixture was heated for 6 hours on a steam bath and concentrated to dryness. The residue was taken up in 50 ml of water and neutralized with potassium carbonate and the resulting solid precipitate was collected by filtration to give, after recrystallization from acetonitrile, 450 mg of the title compound as a light tan powder (21.8% yield); m.p. 267°–269° C.

EXAMPLE 3

(a) 4-Bromo-2-ethylpyridine

4-Amino-2-ethylpyridine (18 g) was dissolved with warming in 48 ml of 48% hydrogen bromide. The solution was cooled to 0° C. and 15 ml of bromine was added dropwise followed by a solution of 25.4 g of sodium nitrite in 37 ml of water over ½ hour while maintaining the temperature below 5° C. The mixture was allowed to warm to room temperature over 2 hours and was then poured onto ice and made alkaline with 35% sodium hydroxide. The aqueous mixture was extracted three times with 200 ml of methylene chloride, the extract was concentrated and the residue was taken up in diethyl ether. The ether solution was dried over magnesium sulfate and concentrated in vacuo at below 40° C. to give, after chromatography (silica gel; 70:30 hexane-ether), 4.1 g of the title compound as an orange oil.

(b) 2-Ethyl-4-(tributylstannyl)pyridine

The title compound (5 g as a yellow oil) was obtained from 3 g of 4-bromo-2-ethylpyridine from (a) above, 6.4 ml of n-butyllithium and 4.3 ml of tributyltin chloride with 50 ml of diethyl ether as solvent by a procedure analogous to that of Example 2(b) above.

(c) (S)-10-(2-Ethyl-4-pyridinyl)-9-fluoro-2,3-dihydro-3-methyl-7-oxo-7H-pyrido[1,2,3-de][1,4]benzoxazine-6-carboxylic acid [I; $R_1$ and $R_2=H$, $R_3=C_2H_5$, $X=O$]

The title compound [1.2 g (49.9% yield); m.p. >300° C. when recrystallized from methyl alcohol] was obtained from 2.5 g of a mixture of the ethyl and butyl ester of (S)-10-bromo-9-fluoro-2,3-dihydro-3-methyl-7-oxo-7H-pyrido[1,2,3-de][1,4]benzoxazine-6-carboxylic acid (2.5 g) (prepared by a procedure analogous to that described in Example 2(c) above), 2.95 g of 2-ethyl-4-(tributylstannyl)pyridine from (b) above, 260 ml of dichloro(triphenylphosphine)palladium in 2.5 ml of dimethylformamide followed by treatment of the mixed ethyl and butyl ester of the title compound so obtained with 25 ml of 2N hydrochloric acid using procedures analogous to those in Example 2(d) above.

EXAMPLE 4

(S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid 1-oxide [I; $R_1=H$, $R_2$ and $R_3=CH_3$, $X=S=O$]

(S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid (U.S. Pat. No. 4,839,355, Example 7f) (192 mg) and 153.7 mg of a mixture of potassium monopersulfate, potassium hydrogen sulfate and potassium sulfate (mole ratio 2:1:1) (Oxone ®) (0.5 mM of potassium monopersulfate) in 20 ml of aqueous propionic acid (20% water) were combined at 0° C. with stirring. The mixture was allowed to come to room temperature, stirred for 4 hours and concentrated to dryness. Saturated sodium chloride solution was added to the mixture which was then extracted with chloroform. The chloroform extract was dried over sodium sulfate and concentrated to dryness. The resulting residue was treated with ethyl alcohol to give 60 mg (30% yield) of the title compound as a solid which was collected by filtration; m.p. 294.0°–295.0° C.

The compounds of Examples 1(b), 2(d), 3(c) and 4 above are novel compounds of the invention.

Examples 5, 6 and 7 below identify known compounds within the scope of the method of the invention. These compounds and their preparation are described in U.S. Pat. No. 4,839,355.

EXAMPLE 5

(S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid [I; $R_1=H$, $R_2$ and $R_3=CH_3$, $X=S$]

EXAMPLE 6

(S)-10-(2,6-Dimethyl-4-pyridinyl)-8,9-difluoro-3-methyl-7-oxo-2,3-dihydro-7H-pyrido[1,2,3-de][1,4]benzoxazine-6-carboxylic acid [I; $R_1=F$, $R_2$ and $R_3=CH_3$, $X=O$]

EXAMPLE 7

(S)-10-(2,6-Dimethyl-4-pyridinyl)-9-fluoro-3-methyl-7-oxo-2,3-dihydro-7H-pyrido[1,2,3-de][1,4]benzoxazine-6-carboxylic acid [I; $R_1=H$, $R_2$ and $R_3=CH_3$, $X=O$]

The intermediate 2-$R_2$-6-$R_3$-4-(tributylstannyl)pyridine used in the preparation of the novel compounds of the invention can be prepared by a sequence of steps from the corresponding 2-$R_2$-6-$R_3$-pyridines, a generically known class of compounds, using well-known procedures. Thus the 2-$R_2$-6-$R_3$-pyridine is converted to the corresponding pyridine N-oxide by peracid oxidation, e.g., with peracetic acid, which then is nitrated with nitric acid to the corresponding 4-nitropyridine N-oxide. The latter compound is reacted with acetyl bromide followed by phosphorus tribromide to provide the corresponding 4-bromopyridine or, alternatively, is hydrogenated over palladium catalyst to give the corresponding 4-aminopyridine which then is converted to the corresponding 4-bromopyridine via the corresponding 4-diazopyridine by reaction with sodium nitrite and aqueous hydrogen bromide, or alternatively, with n-butyl nitrite and cupric bromide. The corresponding 2-$R_2$-6-$R_3$-4-(tributylstannyl)pyridine is prepared from the corresponding 4-bromopyridine by tin-coupling with tributyltin chloride in the presence of a palladium complex catalyst.

The compounds according to the invention were found to be inhibitors of mammalian topoisomerase II when tested in vitro, as described hereinafter, thus indicating their use as cytotoxic and antineoplastic agents in the chemotherapy of cancer in mammals.

Mammalian Topoisomerase II Inhibition Assay Procedure

The inhibition of human topoisomerase II (hereafter topo II) was quantitated by a procedure adapted from that described by Trask et al., EMBO J., 3, 671–676 (1984). The assay quantitates the amount of topo II covalently complexed by DNA at equilibrium during a topo II reaction. This assay determines the potential of a compound to stabilize this complex, which potential is closely related to the cytotoxicity of the compound.

Topo II was purified from late log phase suspension cultures of HeLa WIS by an adaption of the method described by Per et al., Mol. Pharmacol., 32, 17–25 (1987).

Assays (in duplicate) were assembled at 4° C. Assay mix (25 μl) was distributed in Beckman (No. 265270) 1.5 ml microtitre tubes followed by the addition of 5 μl test compound to yield the final concentrations of assay components:
50 mM Tris-Cl pH 7.9
44 mM NaCl
10 mM $MgCl_2$
0.6 mM DTT
0.5 mM EDTA
30 μg/ml BSA
0.5 mM ATP
5.5% (w/v) glycerol
4 ng 3' end labeled (32p) pBR322 DNA ($10^7$ DPM/μg)
10 units Topo II.

The assay mix including the test compound was incubated for 20 minutes at 37° C. The reaction was terminated at 37° C. by the addition of 3 μl 10% SDS followed by the addition of 266 μl 10 mM Tris-Cl pH 7.5, 20 μg/ml BSA, 20 μg/ml calf thymus DNA, 1% SDS.

A SDS/protein precipitate was formed by the addition of 28 μl 2.5M KCl followed by chilling on ice for a minimum of 10 minutes. The precipitate was collected and washed with a Brandell cell harvester on a GFB glass fiber filter membrane as follows. The contents of the assay tube were drawn up into the harvester. The tube was then rinsed 7× with 10 mM Tris-Cl pH 7.5, 1 mM EDTA and 100 mM KCl. The precipitate was washed with 1 L of a solution of 10 mM Tris-Cl pH 7.5, 1 mM EDTA, 100 mM KCl followed by 1 L of 95% ethyl alcohol and finally 0.5 L 70% of ethyl alcohol (per 48 samples in each case). After drying, CPM was determined by liquid scintillation counting with 5 ml Biofluor (NEN Research Products) or Readisafe (Beckman Instruments Inc.) cocktail.

Preparation of test compound—A stock solution (6 mg/ml) of test compound was prepared either in 0.1N sodium hydroxide or 0.2N hydrogen chloride. This solution then was diluted 1/5 into water and serially thereafter in either 0.02N sodium hydroxide or 0.04N hydrogen chloride, respectively. The stock solution and serial dilution of the test compound was stored at −20° C. prior to testing.

Screening of test compound—As an initial screen, the test compound was tested at a final concentration of 2, 20 and 200 μg/ml. The compound was then retested at a range of concentrations (usually 2–3× steps) bridging their approximate $EC_{50}$s, as estimated by the prescreen.

Controls—A solvent control which indicates the base level of topo II-DNA complex formed in the absence of the test compound was included in each test. A control, in which topo II was omitted, was included for each test compound at the highest drug concentration tested.

Reference agent—A dose response curve with mAMSA at 0.01, 0.08, 0.16, 0.32, 1.0 and 10 μg/ml was included in each test.

Data reduction—The $EC_{50}$ (effective concentration at which 50% of the maximal DNA-topo II complex is formed) of a test compound is defined to be the concentration with activity equal to the $EC_{50}$ of the reference agent, mAMSA. The maximal DNA-topo II complex formed is taken as that equal to that formed at the nearly saturating dose of mAMSA (10 μg/ml).

The results obtained for representative compounds of the invention in the human topoisomerase II assay procedure expressed as $EC_{50}$s (μM) are presented in Table I below.

TABLE I

| Example | $EC_{50}$ (μM) |
| --- | --- |
| 1(b) | 57 |
| 2(d) | 68 |
| 3(c) | 92 |
| 4 | 62 |
| 5 | 9.4 |
| 6 | 50 |
| 7 | 31 |

(S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid (Example 5) was tested for antitumor activity in mice against several tumor systems, as described more fully below, and was found to possess antineoplastic activity as evidenced by its activity in reducing the size of and curing tumors, and increasing the survival time of the mice.

In vivo Antitumor Assay Procedure

Mice: Inbred: C3H/He; and Hybrids: B6D2F1 (C57BL/6 females×DBA/2 males), CD2F1 (Balb/c females×DBA/2 males) and B6C3F1 (C57BL/6×C3H) were bred at Wayne State University from strains obtained from the Frederick Cancer Research Facility, Frederick, Md. or from commercial suppliers.

Tumors: Murine Tumors: P388 leukemia and the following transplantable solid tumors of mice were used for in vivo testing: B16 melanoma, pancreatic ductal adenocarcinoma No. 03, colon adenocarcinoma No. 38 and mammary ductal adenocarcinoma No. 16/C. All tumors are in the Developmental Therapeutics Program frozen tumor repository, maintained by the Biological Testing Branch, Frederick, Md. Each has a detailed description, code identification number, and list of references at the National Tumor Repository. Tumors were maintained in the mouse strain of origin and were transplanted in the appropriate F1 hybrid (or the strain of origin) for therapy trials. The mice were supplied food and water ad libitum.

In vivo Studies

Chemotherapy: For pancreatic ductal adenocarcinoma No. 03, colon adenocarcinoma No. 38, and mammary ductal adenocarcinoma No. 16, the following methods were used to help ensure a more uniform tumor burden per mouse (thus reducing the requirement for greater numbers of mice per group), bilateral tumor implants were used. The animals necessary to begin an experiment were pooled, implanted bilaterally s.c. on day zero with 30-60-mg tumor fragments using a 12-gauge trocar, and again pooled before randomization to the various treatment and control groups. Chemotherapy was started within three days after tumor implantation while the number of cells per mouse was relatively small ($1 \times 10^7 - 1 \times 10^8$ cells).

For P388 leukemia and B16 melanoma studies the tumor cells were implanted IP on day zero and treatment was started on day one (also IP). Titered controls were also included to facilitate the calculation of tumor cell kill.

End Points for Assessing Antitumor Activity: Quantitative end points used to assess antitumor activity included % Increased Life Span (% ILS), Tumor Cell Kill ($Log_{10}$ kill), and Tumor Growth Inhibition (T/C). Long Term Survivors (45 or 60 day) were excluded from calculations of % ILS and Tumor Cell Kill.

Endpoints were calculated as follows:

% ILS:

$$\% \; ILS = \frac{D_t - D_c}{D_c} (100)$$

where $D_t$ is the median day of death for treated and $D_c$ is the median day of death for control groups.

Tumor Cell Kill

The $log_{10}$ cell kill was calculated from the following formula:

$$Log_{10} \; kill \; (total) = \frac{T - C}{(3.32)(Td)}$$

where T−C is the tumor difference in the median day of death between the treated (T) and the control (C) groups and Td is the tumor doubling time (in days), the latter estimated from the best fit straight line from a log-linear growth plot of the control-group tumors in exponential growth. The conversion of the T−C values to $log_{10}$ cell kill is possible because the Td for tumors regrowing post-treatment approximated the Td values of the tumors in untreated control mice.

T/C Value: Tumors were measured with a caliper once or twice weekly (as needed) until either tumors exceeded 1600 mg or cure was assured. Tumor weights were estimated from two-dimensional measurements: Tumor Weight (mg)=$(a \times b^2)/2$, where a and b are the tumor length and width (mm), respectively. Measurements were carried out simultaneously in both the treatment and control groups. When the control group tumors reached approximately 750-1500 mg in size (median of group), the median tumor weight of each group was determined (including zeros). The T/C value in percent is an indication of antitumor effectiveness. A T/C equal to or less than 42% is considered significant antitumor activity. A T/C value <10% is indicative of a high degree of antitumor activity and is the level used by National Cancer Institute to justify further development if other requirements are met (termed DN-2 level activity).

ACTIVITY

All the trials are summarized in Table II. By DTP-NCI standards, a T/C $\leq$42% is considered active and a T/C $\leq$10% is considered highly active.

TABLE II

In vivo Antitumor Activity of the Compound of Example 5

| Tumor | Drug Route[1] | Schedule | Maximum Tolerated Total Dose (mg/kg) | T/C | % ILS | Long Term Survivors |
|---|---|---|---|---|---|---|
| Panc03 (SC) | SC[2] | QD3-9 | 781 | 17% | — | 0/5 |
| Colon 38 (SC) | SC[2] | QD3-9 | 504 | 0% | — | 1/5[4] |
| Mam16/C (SC) | SC[2] | QD1-4 | 263 | 15% | — | 0/5 |
| P388(IP) ($10^6$ cells) | IP[2] | QD1-7 | 504 | — | 92% | 0/5 |
| P388(IP) ($10^6$ cells) | IP[3] | QD1,5,9 | 1014 | — | 90% | 0/6 |
| B16(IP) (0.5 ml 10% brie) | IP[3] | QD1,5,9 | 1500 | — | 66% | 1/6[5] |

[1]Drug route; SC behind neck
[2]Vehicle = 3% EtOH, 3% NaHCO$_3$, 1% polysorbitan-40 (tween-40); (pH adj to pH 7 with 1N HCl); suspension
[3]Vehicle = 5% EtOH, 1% NaHCO$_3$, 0.3% polysorbitan-40 (tween-40) (pH 8.3); suspension
[4]Cure; no tumor evident; day 119
[5]Day 60; tumor evident The data summarized in Table II establish the following. The compound of Example 5 is clearly active against the three solid tumors evaluated (Pancreatic Ductal Adenocarcinoma 03, Colon Adenocarcinoma 38, and Mammary Adenocarcinoma No. 16/C). Furthermore, it is highly active against Colon Adenocarcinoma No. 38, and demonstrated good activity (66% ILS, 2.0 $log_{10}$ tumor cell kill) against B16 melanoma IP. Against P388, DTP-NCI considers a % ILS of >25% as active. With the compound of Example 5, a 90% ILS was obtained, which is equal to 5.2-7.0 $log_{10}$ tumor cell kill. This is excellent activity for this tumor model.

Dose limiting toxicity appeared to be leukopenia, based on small spleen sizes in necropsy of mice dying at lethal dosage levels. The compound of Example 5 was well tolerated with no long delayed toxicity problems. Host recovery was rapid, with mice regaining their lost body weight within two to five days post nadir (at the highest non-toxic dosage levels).

In practicing the method of the invention, the therapeutic dose of the compound of formula I to be administered to the mammal afflicted with malignant cells is that amount which is effective to inhibit mammalian topoisomerase II and thereby to inhibit the growth of, kill or induce the regression of the malignant cells, or to prolong the life of the mammal.

The specific amount of the compound of formula I constituting a therapeutically effective dose and the length of treatment required will vary since it is dependent on a number of factors such as, for example, the size, age, condition and species of the mammal to be treated, the degree of involvement of the malignancy, the specific compound to be administered and its bioavailability, the dose regiment and the mode of administration. The specific amount to be employed for a particular afflicted mammal is readily determinable by the skilled artisan using conventional techniques.

In practicing the invention, the compounds can be administered to the mammal orally or parenterally.

The compounds can be prepared for use by incorporating them in conventional, pharmaceutically acceptable, diluents, carriers or excipients. For parenteral administration (intravenous, intraperitoneal, subcutaneous or intramuscular), the compounds are dissolved or suspended in an aqueous or non-aqueous vehicle. For oral administration, the compounds are formulated in dosage unit form as tablets or capsules. Exemplary diluents, carriers or excipients include lactose, dextrose, sucrose, sorbitol, mannitol, starches, gum acacia, calcium phosphate, mineral oil, cocoa butter, alginates, tragacanth, gelatin, methyl cellulose, methyl and propyl hydroxybenzoates, talc, magnesium stearate and the like.

We claim:

1. A method of inhibiting mammalian topoisomerase II in a mammal which comprises administering to the mammal a compound which is a (S)-3-methyl-7-oxo-2,3-dihydro-7H-pyrido[1,2,3-de][1,4]benzoxazine or -benzothiazine of the formula

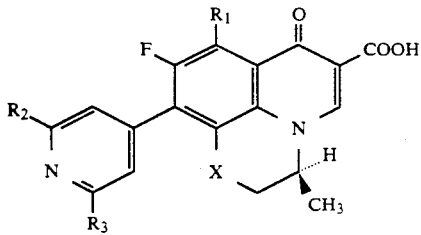

wherein $R_1$ is hydrogen or fluoro, $R_2$ and $R_3$ each independently is hydrogen or alkyl having 1 to 4 carbon atoms, and X is O, S or S=O; a pharmaceutically acceptable acid-addition salt thereof; or a salt thereof with a pharmaceutically acceptable cation; the compound being administered in a therapeutic amount which is effective to inhibit the mammalian topoisomerase II.

2. A method according to claim 1 wherein X is S.

3. A method according to claim 1 wherein $R_2$ and $R_3$ independently are hydrogen, methyl or ethyl.

4. A method according to claim 3 wherein X is S.

5. A method according to claim 4 wherein $R_1$ is hydrogen.

6. A method according to claim 5 wherein the compound is (S)-10-(2,6-dimethyl-4-pyridinyl)-9-fluoro-3-methyl-7-oxo-2,3-dihydro-7H-pyrido[1,2,3-de][1,4]benzothiazine-6-carboxylic acid; a pharmaceutically acceptable acid-addition salt thereof; or a salt thereof with a pharmaceutically acceptable cation.

7. A method according to claim 3 wherein the compound is selected from the group consisting of (S)-10-(4-pyridinyl)-9-fluoro-2,3-dihydro-3-methyl-7-oxo-7H-pyrido[1,2,3-de][1,4]benzoxazine-6-carboxylic acid, (S)-10-(2-ethyl-6-methyl-4-pyridinyl)-9-fluoro-2,3-dihydro-3-methyl-7-oxo-7H-pyrido[1,2,3-de][1,4]benzoxazine-6-carboxylic acid, (S)-10-(2-ethyl-4-pyridinyl)-9-fluoro-2,3-dihydro-3-methyl-7-oxo-7H-pyrido[1,2,3-de][1,4]benzoxazine-6-carboxylic acid, (S)-10-(2,6-dimethyl-4-pyridinyl)-9-fluoro-3-methyl-7-oxo-2,3-dihydro-7H-pyrido[1,2,3-de][1,4]benzothiazine-6-carboxylic acid 1-oxide, (S)-10-(2,6-dimethyl-4-pyridinyl)-9-fluoro-3-methyl-7-oxo-2,3-dihydro-7H-pyrido[1,2,3-de][1,4]benzothiazine-6-carboxylic acid, (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylic acid, (S)-10-(2,6-dimethyl-4-pyridinyl)-9-fluoro-3-methyl-7-oxo-2,3-dihydro-7H-pyrido[1,2,3-de][1,4]benzoxazine-6-carboxylic acid;

a pharmaceutically acceptable acid-addition salt thereof; or a salt thereof with a pharmaceutically acceptable cation.

* * * * *